United States Patent [19]
Hildebrandt

[11] Patent Number: 4,524,774
[45] Date of Patent: Jun. 25, 1985

[54] APPARATUS AND METHOD FOR THE STIMULATION OF A HUMAN MUSCLE

[75] Inventor: Jürgen Hildebrandt, Munich, Fed. Rep. of Germany

[73] Assignee: Deutsche Nemectron GmbH, Karlsruhe, Fed. Rep. of Germany

[21] Appl. No.: 399,283

[22] Filed: Jul. 19, 1982

[30] Foreign Application Priority Data

Jul. 30, 1981 [DE] Fed. Rep. of Germany ....... 3130104

[51] Int. Cl.³ ............................................. A61N 1/36
[52] U.S. Cl. .................................... 128/421; 128/903
[58] Field of Search ............... 128/419 E, 419 R, 421, 128/422, 423 W, 903

[56] References Cited

U.S. PATENT DOCUMENTS

| 3,204,637 | 9/1965 | Frank et al. | 128/423 W |
|---|---|---|---|
| 3,572,316 | 3/1971 | Vogelman et al. | 128/903 |
| 3,662,758 | 5/1972 | Glover | 128/903 |
| 3,727,616 | 4/1973 | Lenzkes | 128/419 E |
| 4,390,023 | 6/1983 | Rise | 128/421 |

FOREIGN PATENT DOCUMENTS 2803366 7/1978 Fed. Rep. of Germany.

OTHER PUBLICATIONS

Silverman et al., "IEEE Transactions on Biomedical Electronics", vol. 22, No. 3, May 1975, pp. 207-212.
Proceeding of the 5th International Conference on Medical Physics and 12th International Conference on Medical and Biological Engineering; Jerusalem, Israel, 1979.
Advances in External Control of Human Extremities, Proceedings of the 7th International Symposium on External Control of Human Extremities, Dubrovnik, Sep. 7-12, 1981.

Primary Examiner—William E. Kamm
Attorney, Agent, or Firm—Sandler & Greenblum

[57] ABSTRACT

Apparatus and process for stimulating muscle such as where a portion of a muscle and its nerve structure are damaged. Muscle stimulators are embedded within the muscle at the general location where the muscle is to be activated. Muscle stimulation signals are transmitted to the muscle stimulators by a transmitter-receiver which receives muscle potential signals from muscle potential sensors embedded within the muscle, and converts these signals into muscle stimulation signals. The transmitter-receiver may be mounted on a cuff which can be externally secured. The cuff, the stimulators, and sensors are provided with antennas such that the transmitter-receiver transmits and receives signals without being wired to the sensors and stimulators. The sensors and stimulators have power supplies which may be energized from external high frequency sources which may themselves be mounted on the cuff. Power transmission occurs through antennas such that the sources need not be wired to the various components.

28 Claims, 4 Drawing Figures

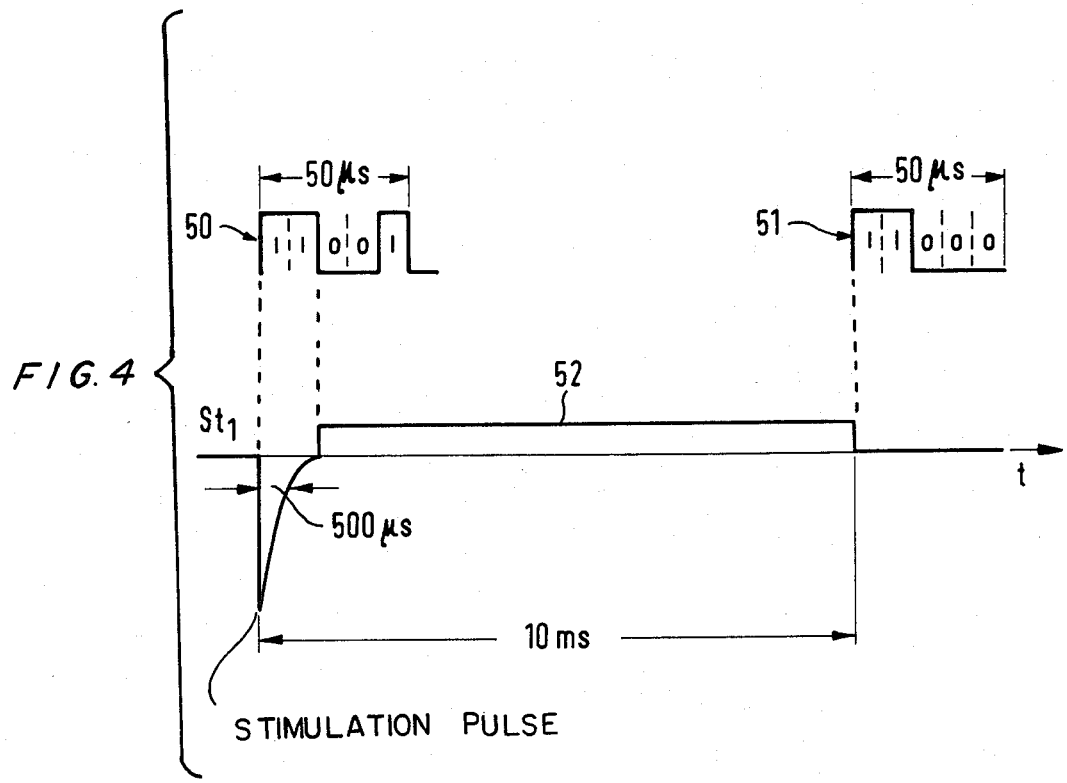

APPARATUS AND METHOD FOR THE STIMULATION OF A HUMAN MUSCLE

BACKGROUND OF THE INVENTION

The present invention relates to an apparatus for stimulation of a muscle in the human body using at least one stimulus producer designed to be implanted in the muscle, a receiver and a power supply for the receiver, a number of electrodes for output of stimulation signals and for the supply to the muscle at different points thereof of stimulus pulses which are exactly defined with respect to the order, the amplitude, the length and form of the pulses, such pulses causing a muscle contraction which takes place as naturally as possible.

Such an apparatus may be used, more speciallly, for overcoming signs of paralysis or the like which are physiological in nature. A programmable stimulation apparatus for human tissue has been designed in the prior art, in the case of which, using an external controller and an implanted receiver, stimulus signals are produced in a cyclical order (as preprogrammed by the stimulus producer) at a number of electrodes implanted at positions in the tissue, where stimulation is to take place, such electrodes being wired up with the stimulus producer. With such a system, after writing a program, it is possible to make a desired motion of the muscles for a certain form of motion of the body to take place by operation of a switch and such motion may be repeated. By "patching" the program, changed muscular motion may be produced. Not only for starting the muscle reaction, but furthermore controlling it as it takes place, switching or adjustment parts have to be worked by the patient or his doctor. Furthermore, wires, which have to be implanted, for joining the stimulus electrodes with the stimulus producer are likely to break down after being used for a long time. A patient with the known apparatus is furthermore only able to take a small controller around with him to be used. Furthermore, its stimuli produced causing motion are very limited and, in fact, more complex motions may only be produced by a stationary controller which is not able to be moved. The circuit of this known apparatus is covered by a detailed account given in German Offenlegungsschrift specification 2,803,366. The known apparatus is, generally speaking, such that its operation is very limited if it is a question of producing voluntary motion of the muscles.

GENERAL OVERVIEW OF THE INVENTION

Unlike this prior art, one purpose of the present invention is that of designing an apparatus of the sort noted in such a way that a voluntary, free function is possible without hand operation.

A further purpose of the invention is designing such an apparatus which does without wires implanted into the muscle while nevertheless making certain that the stimulus or stimulation electrodes are within the full control of the patient.

For effecting this purpose, and further purposes, an apparatus for the stimulation of a human muscle having stimulus producers designed to be implanted in said muscle, a receiver and a power supply for the receiver and a number of electrodes for output of stimulus signals, is characterized in the present invention inasfar as it has:

(a) a number of separate stimulus producers, designed to be implanted in a muscle, having electrodes and each stimulus producer has a receiver, designed for selectively receiving a signal, a stimulus generator, whose stimulus signal is controlled in its amplitude frequency and length by way of a received signal, and a power supply, the power supply being itself supplied with received high-frequency energy, (b) muscle potential sensors, designed to be implanted in the muscle, of which each has a transmitter, designed for transmitting a signal which is modulated to be representative of sensed muscle potential and may be selectively translated, each such transmitter having a power supply which is as well supplied with received high-frequency energy, and (c) a telemetry receiver designed for use with the transmitters of the muscle potential sensors and for modulation, by way of a data processing circuit, of a telemetry transmitter designed for use with the stimulus producers.

It will be seen from this that the general process and method of use teaching of the invention is a new method of muscle stimulation using a number of muscle potential sensors, implanted at a number of different points in the muscle, the separate muscle potentials are measured and sent by way of transmitters (which are best integrated with the muscle potential sensors) to a telemetry receiver, the received signals are translated in a data processing circuit and the translated or processed signals are transmitted by way of a telemetry transmitter to a number of stimulus producers which as well are implanted at spaced points in the muscle, such stimulus producers outputting stimulus pulses by way of electrodes.

It will be seen that the invention makes use of sensors for measuring the muscle potentials and on the basis of such measured muscle potentials, operation of the stimulus producers takes place and the muscle motion is caused by way of stimulus electrodes which are selectively and definedly supplied with physiological or programmable stimulus signals in a way dependent on the measured muscle potentials. Because of the use of sensors, there is no need for hand control, even if such control takes place by way of example through an external computer and furthermore the parts of a motion of the muscle are controlled in a way dependent on the electrophysiological conditions of the muscle, in which respect, more specially because of the number of separate stimulus producers, there is the best possible matching, and the best possible range of motion steps. It is not necessary to have further connection wires between the stimulus producers and the electrodes; the electrodes may be joined up directly with the stimulus producers.

As part of a preferred development of the invention, the power supplies are themselves powered with the transmission energy of the telemetry transmitter. As a general teaching of the invention, however, the power supplies of the stimulus producers and the muscle potential sensors may get their energy or power from separate energy transmitters, something which, however, would have the effect of increasing the price of the apparatus, such an increase in price being made unnecessary, as a further useful effect, by the said design of the apparatus of the invention.

As part of an other preferred form of the invention the transmitters of the muscle potential sensors and the telemetry receivers are designed for use on a different frequency band to a frequency band used by the receivers of the stimulus generators and the telemetry transmitter, this separating, in a trouble-free way, the untranslated signals from the muscle potential sensors and the signals, after being translated, sent out by the telemetry transmitter for the receivers of the stimulus generators so that, in a trouble-free way, there will be no interference or interaction in the case of the two sorts of signals.

As part of a further preferred form of the invention, the antennas of the telemetry receiver and of the telemetry transmitter are housed in a unit designed to be seated on a limb having the muscle to be stimulated so that the limb is at least partly covered thereby.

In this respect, a possible further development of the invention in this connection is for the antennas of the telemetry receiver and transmitter have a belt, which may be placed round the limb. This is responsible for comfort of a patient supporting the external, not implanted parts of the apparatus on his body.

DETAILED ACCOUNT OF WORKING EXAMPLE OF THE INVENTION

Further details and useful effects of the invention are to be seen from the claims and the account now to be given, based on the diagrammatic figures, of one working example of the invention.

FIG. 4 is a graph, by way of example, of a train of pulses as a way of encoding information for the stimulus producers, to make clear changes in the voltage of the electrode of one such stimulus producer.

Figure 1:
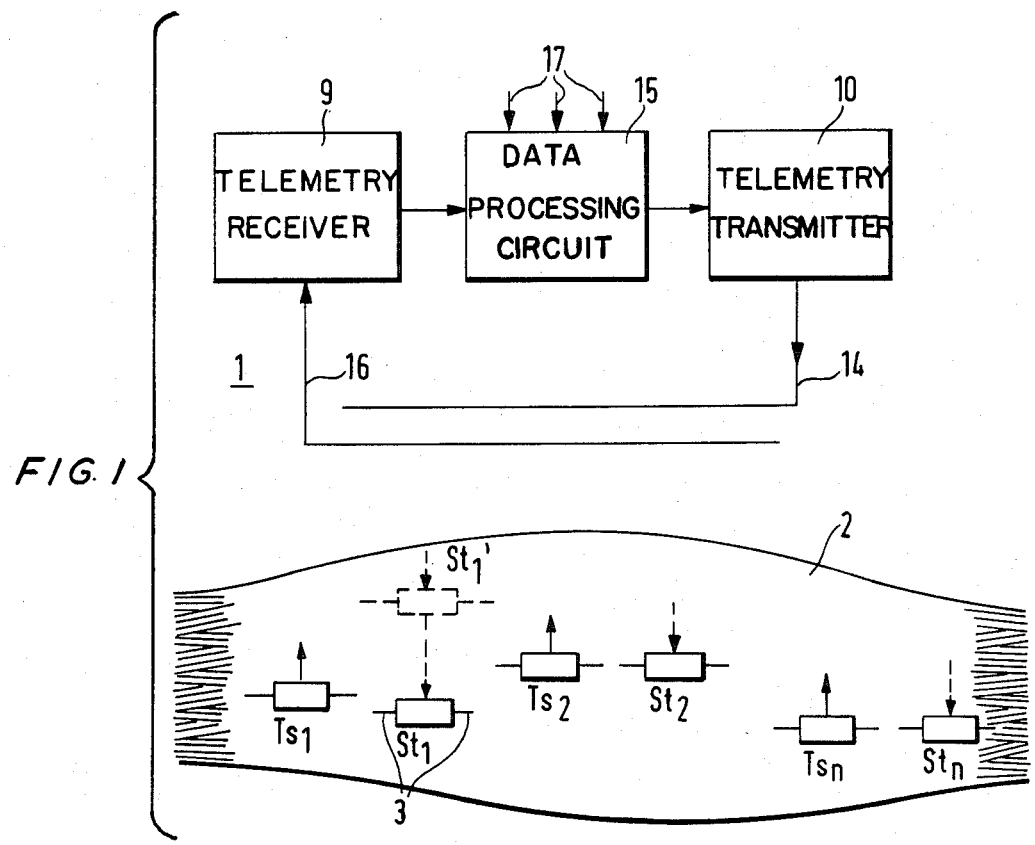
FIG. 1 is a block diagram of the complete apparatus at a diagrammatic view of a muscle.
Figure 2:
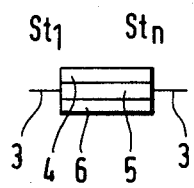
FIG. 2 is a cross-section through a stimulus producer forming part of the apparatus.
Figure 3:
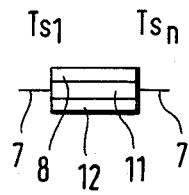
FIG. 3 is a cross-section through a muscle potential sensor of the apparatus.

In FIG. 1 it will be seen from block diagram 1 that for the stimulation of a human muscle 2, that stimulus producers $St_1$ to $St_n$ are implanted at any desired positions in the muscle, each stimulus producer having its muscle potential sensors $Ts_1$ to $Ts_n$ for use therewith and which, as well, are implanted in the muscle so that it is possible to say that one given muscle potential sensor Ts and one stimulus producer St take the form of a functional unit which may be put into operation selectively using parts of the apparatus still to be detailed. It would furthermore be possible, in case of need, for a number of stimulus producers $St_1'$ to $St_n'$ of the same design to be used with one muscle potential sensor Ts or for a number of muscle potential sensors $Ts_1$ to $Ts_n$ to be used with a single stimulus producer St, sensors Ts and stimulus producers St, which are designed for use together being joined together, more specially by being placed in a common housing. Not only the stimulus producers St, but furthermore the muscle potential sensors Ts may be placed anywhere desired by the patient's doctor. They are leadless, that is to say the stimulus electrodes 3 and the sensor electrodes 7 are placed right on or next to the stimulus producer St or, in the other case, the sensor Ts (see furthermore FIGS. 2 and 3). The stimulus producers St are supplied by way of a telemetry transmitter 10, of which a more detailed account will be given, with modulated high-frequency energy, such energy meeting the energy need of the receiver 4 and the stimulus generator 5 as well by way of an integrated power supply 6 within the stimulus producer St. In place of keeping to the design to be seen in the figure, it is possible in the case of one working design of a stimulus producer St for the receiver 4, the stimulus generator 5 and the power supply 6 to be in the form of a single IC as may be known to those trained in the art, the receiving circuit of such IC having an antenna tuned to the frequency of the telemetry transmitter 10.

The further muscle-implanted potential sensors $Ts_1$ to $Ts_n$ have sensor electrodes 7 by way of which muscle potentials, still produced in a muscle with a damaged nerve, may be sensed at given points, such muscle potentials being translated by way of an amplifier and modulator 11 to control signals for a telemetry transmitter 8 integrated in a muscle potential sensor Ts. On the same lines as the stimulus producers St, the muscle potential sensors Ts have a power supply 12, which itself gets power by way of a receiver for use therewith or by way of a telemetry transmitter 8 (designed as a transmitter-receiver) from the external telemetry transmitter 10. The account so far given on the design of the stimulus producers St is true in this respect as well, i.e. it goes for this part of the system.

For operation of the implanted stimulus producers St and the implanted muscle potential sensors Ts, use is made of a telemetry transmitter 10 of generally known construction, whose transmitting antenna 14 is placed in a belt or cuff, placed round the muscle 2, i.e. the limb of which it is part, such belt not being detailed in the figures to make them simpler. It is furthermore possible for the transmitting antenna 14 to be placed in a shell, for example in the form of a hollow ball which may be placed in the seat of the user's pants, such a hollow part of a ball furthermore having a transmitting antenna 16 for a telemetry receiver 9, or, in place of this, an antenna which may be switched over for the two uses in a known way. The telemetry receiver 9, the transmitter 10 and a data processing circuit 15 may, like a battery, be supported on a normal belt and are joined up by way of a coaxial cable with antennas 14 and 16.

The telemetry transmitter 10 sends out signals which are selectively received by the stimulus producers $St_1$ to $St_n$, the transmitted power or energy of the telemetry transmitter 10 in the times between signals being used for supplying the power supplies 6 and 12 of stimulus producers $St_1$ to $St_n$ and of the muscle potential sensors $Ts_1$ to $Ts_n$ with power, the high-frequency output of the transmitter being rectified and stored.

The control of the telemetry transmitter 10 and its modulation is by way of a data processing circuit 15, whose main part may be a microprocessor and in which the signals, received by way of a telemetry receiver 9 from the transmitters 8 of the muscle potential sensors Ts are translated or processed for driving the telemetry transmitter 10.

The data processing circuit 15, controlling the transmitter 10, is responsible in an encoding stage for forming amplified and addressed single signals from the signals of the telemetry receiver 9, which, for its part, is responsible for demodulating and decoding all of the signals of the signal train coming in from the transmitters 8 of the muscle potential sensors Ts. For making a further form or development of such single signals, which is possibly desired for therapeutic purposes, the data processing circuit 15 has inputs 17 for control voltages, which the patient or his doctor may in addition make use of to have an effect on the amplitude, length and/or form of the pulses. With the help of the addressed and shaped single signals, the telemetry transmitter 10 is so controlled that signals, proportional to the single signals, are selectively sent to the stimulus producers. In the receiver 4 of the stimulus producer St, for example, a modulated RF signal, transmitted by the telemetry transmitter 10, is received. The information of the signal is used for producing stimulus pulses in the stimulus generator 5 and output of the same by way of the electrodes 3. The information may, in each case, be made up of a 5 bit long code-word 50, 51 in each case with a length of 50 microseconds for example, see FIG. 4. Such a form of encoding may be used for an 8-channel apparatus, that is to say one having up to 8 stimulus producers St. The first bit is for synchronization. The next three bits are used for selection of the desired stimulus producer St in the information transmission system and the last bit is used for controlling the output of a stimulus pulse. The line-up between parts of the code to be seen in one example of FIG. 4. The serial bit train is taken up in a shift register after the start pulse has been produced by the sync bit. The code-word undergoes comparison with the permanently wired code and if the read signal is the same as the permanently wired one, the stimulus producer St in question will be used and the output flipflop will be switched, that is to say into the "on" or the "off" condition, dependent on if the last bit is a "1" or a "0". When the output is changed over from 0 to 1, a stimulus or stimulation pulse is produced with a length of for example 500 microseconds and then, by way of the power supply, a storage capacitor is charged up by way of a constant current supply till the charging operation is interrupted after for example 10 milliseconds by the "off" command. In this respect, in the charging stage, there will be a constant voltage 52 at the electrode 3 of the stimulus producer (in the present case $St_1$ in question. The actual value of the constant voltage 52 will be dependent on the size of the tissue resistance. As a general point, forms of the apparatus with up to 100 and more channels are possible. The apparatus to be seen in the figures and of which an account has been given is only one of a number of possible forms giving useful effects.

The power supply for the stimulus producers $St_1$ to $St_n$ and of the muscle potential sensors $Ts_1$ to $Ts_n$ by way of the power supplies 6 and 12 is best taken care of in the modulation intervals of the telemetry transmitter 10. The separate electronic circuits may, as a general point, be designed as in the prior art.

It has been seen from experience on using the apparatus that for one telemetry transmitter 10 a frequency of 27.12 Mhz with pulse code modulation has the desired properties, the receiver 4 of the stimulus producer St being tuned to this frequency as well. For the transmitters 8 of the muscle potential sensors Ts and the telemetry receivers 9 use was made, for example, of a frequency of 40.68 to 40.75 MHz with a frequency excursion of in each case $8 \times 1$ kHz was selected so that up to eight stimulus producers $St_1$ to $St_8$ might send out correlated stimulus signals selectively under the control of the data processing circuit 15. In this respect it it useful if, in addition, further stimulus producers $St_1$ to $St_1'$ of the same design are used for one single transmission channel of a muscle potential sensor. On the same lines, it is furthermore possible for a number of muscle potential sensors Ts of the same sort to be used with a single stimulus producer St.

In the case of forms of paralysis caused by damage to the CNS and in the case peripheral nerve damage (where use of the invention is more limited), in which case not all nerve conductionpaths are cut so that there are still some pulses under the control of the patient's will, such pulses may be amplified with the apparatus of the invention (unlike the case of prior art forms of apparatus) so that such amplified signals may be supplied to therapeutically selected points on the muscle as a supermaximal stimulus for all the resting motor units taken together.

Such electro-stimulation by using the action potentials still in existence makes it possible, because of the amplification of the separate contractions of the muscle in question, for motions to be produced against the force of gravity or for things to be supported statically, something which has not so far been possible because of the pathologically enfeebled condition of the nerves under the control of the will of the patient.

Furthermore, it is possible, using the apparatus of the invention, for muscles, which have only become temporarily enfeebled, to be stimulated for a long time methodically with a view to restoring the original function without limiting the patient any more with respect to his possible muscle motion or increasing the danger of infection of such a patient.

In this connection, a possible change of methodical "keep-going stimulation" is to be noted, in which, using apparatus of the present invention, muscle parts, which are no longer directly innervated, may be stimulated by intact muscles of the patient till such muscle without innervation may be supplied by the original or new conduction paths because of the healing process or till the "software" has been produced for a cybernetic stimulus system for the patient in question.

I claim:

1. Apparatus for stimulating a muscle, comprising:
   (a) first means for stimulating said muscle, said first means being adapted to receive muscle stimulation signals from third means and to stimulate one region of said muscle accordingly;
   (b) second means for receiving muscle stimulation signals directly from another region of said muscle and transmitting said muscle stimulation signals to said third means; and
   (c) third means adapted to receive said muscle stimulation signals and to re-transmit said muscle stimulation signals to said means for stimulating said muscle.

2. The apparatus as defined by claim 1 wherein said first means comprises a receiver for receiving said muscle stimulation signals from said third means, and a plurality of electrodes for directly stimulating said muscle.

3. The apparatus as defined by claim 2 wherein said first means further comprises a power supply.

4. The apparatus as defined by claim 3 further comprising an external high frequency energization source to power said power supply of said first means.

5. The apparatus as defined by claim 4 wherein said first means further comprises a plurality of electrodes adapted to be embedded within said muscle to stimulte said muscle.

6. The apparatus as defined by claim 5 wherein said first means further comprises an antenna adapted to receive said muscle stimulation signals from said third means, and an antenna to receive said high frequency energy from said external high frequency energization source.

7. The apparatus as defined by claim 1 wherein said second means comprises at least one electrode adapted to sense said muscle stimulation signals.

8. The apparatus as defined by claim 7 wherein said second means further comprises an antenna connected to transmit said muscle stimulation signals to said third means, and a power supply.

9. The apparatus as defined by claim 8 further comprising an external high frequency energization source to power said power supply of said second means.

10. The apparatus as defined by claim 1 wherein said second means is adapted to transmit said muscle stimulation signals while modulating said signals as a function of sensed muscle potential.

11. The apparatus as defined by claim 10 wherein said first means is further adapted to control the amplitude, frequency and length of the stimulation signal applied to said muscle as a function of the signal received from said third means.

12. The apparatus as defined by claim 11 wherein said third means is configured to receive said stimulation signals from said second means, to translate said stimulation signals, and to re-transmit said translated stimulation signals to said first means.

13. The apparatus as defined by claim 1 wherein the frequencies of said second means transmitter and said third means receiver are different from said receiver of said first means and the transmitter of said third means.

14. The apparatus as defined by claim 1 wherein said third means is mounted on a cuff adapted to be secured externally around the muscle to be stimulated.

15. The apparatus as defined by claim 14 wherein said third means further comprises at least one antenna thereon to transmit and receive a signal to and from said first and second means, respectively.

16. The apparatus as defined by claim 15 wherein said cuff comprises means for securing said cuff around said muscle.

17. The apparatus as defined by claim 1 wherein said third means is not wired to either of said first or second means.

18. Apparatus for stimulating a muscle, comprising:
(a) first means implantable within a first region of said muscle for stimulating said muscle, said first means being adapted to receive a muscle stimulation signal from an external third means and to stimulate one region of said muscle accordingly;
(b) second means implantable within a second region of said muscle to sense muscle stimulation signals directly from said second region of said muscle and transmit said muscle stimulation signals to an external third means; and
(c) third means positioned externally and being adapted to receive said muscle stimulation signals and to retransmit said muscle stimulation signals to said first means for stimulating said muscle.

19. A cuff for use with an apparatus for stimulating a muscle, comprising:
(a) a receiver tuned to receive, demodulate and decode a signal transmitted by an implantable muscle potential sensor, and an antenna for receiving the transmitted signal from the implantable sensor;
(b) data processing means for amplifying and addressing the signals received by said receiver from said implantable muscle sensors;
(c) a transmitter for transmitting the signals of (b) to a muscle stimulator implantable in a muscle to stimulate said muscle; and
(d) means for securing said cuff to a body.

20. The apparatus as defined by claim 19 further comprising control voltage input means whereby the amplitude, duration or form of said signals of step (b) may be modified at will.

21. A process for stimulating a muscle region comprising the steps of:
(a) measuring directly muscle potential at a first muscle region by means of a plurality of muscle potential sensors implanted in a first region of muscle;
(b) transmitting said measured muscle potential to a transmitter-receiver which receives said muscle potential signals and re-transmits these signals as muscle stimulation signals; and
(c) receiving said transmitted measured muscle stimulation signals of step (b) and transmitting the muscle stimulation signals to a plurality of implanted stimulus producers implanted at a second region in the muscle to stimulate the second region of said muscle.

22. The process as defined by claim 21 wherein said second region is connected to said first region by a nerve which has been at least partially damaged.

23. The process as defined by claim 22 comprising energizing said apparatus by high frequency energy generated by an external source.

24. The process as defined by claim 23 comprising performing step (c) external to the body in which the muscle is located.

25. The process as defined by claim 24 further comprising transmitting the stimulation signal of step (c) to a plurality of implanted stimulus producers from a location external to the body in which said muscle is located.

26. The process as defined by claim 21 comprising receiving and transmitting in steps (c) and (d) by using antennas.

27. A process of stimulating damaged muscle tissue where a portion of the muscle nerve structure has been inactivated comprising the steps of:
(a) measuring directly muscle potential at an undamaged muscle region by means of a plurality of potential sensors implanted in a muscle;
(b) transmitting said measured muscle potential to an external transmitter-receiver, receiving said measured muscle potential in said transmitter-receiver and re-transmitting said muscle potential signals as muscle stimulation signals; and
(c) receiving said transmitted muscle stimulation signals of step (b) and transmitting the muscle stimulation signals to a plurality of implanted stimulus producers embedded at an effected region in the muscle suffering from said nerve damage to stimulate the effected region of said muscle.

28. Apparatus for stimulating a muscle, comprising:
(a) first means for stimulating said muscle, said first means being adapted to receive muscle stimulation signals from third means and to stimulate one region of said muscle accordingly;
(b) second means for receiving muscle stimulation signals directly from a region of said muscle and transmitting said muscle stimulation signals to said third means; and
(c) third means adapted to receive said muscle stimulation signals and to re-transmit said muscle stimulation signals to said means for stimulating said muscle.

* * * * *